US006482756B2

(12) United States Patent
Li

(10) Patent No.: US 6,482,756 B2
(45) Date of Patent: *Nov. 19, 2002

(54) METHOD OF RETAINING ANTIMICROBIAL PROPERTIES ON A HALAMINE-TREATED TEXTILE SUBSTRATE WHILE SIMULTANEOUSLY REDUCING DELETERIOUS ODOR AND SKIN IRRITATION EFFECTS

(75) Inventor: Shulong Li, Spartanburg, SC (US)

(73) Assignee: Milliken & Company, Spartanburg, SC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/361,876

(22) Filed: Jul. 27, 1999

(65) Prior Publication Data

US 2002/0090872 A1 Jul. 11, 2002

(51) Int. Cl.$^7$ .................. B32B 27/04; D06M 11/00
(52) U.S. Cl. .................. 442/123; 442/152; 442/164; 442/181; 442/199; 442/304; 442/311; 442/327; 442/361; 442/415; 442/416; 8/115.54; 8/147
(58) Field of Search .................. 8/115.51, 115.54, 8/115.69, 147; 442/123, 152, 164, 181, 199, 304, 311, 327, 361, 415, 416

(56) References Cited

U.S. PATENT DOCUMENTS

| 4,236,891 A | 12/1980 | Scardera et al. ............ 8/108 A |
| 4,395,454 A | 7/1983 | Baldwin ...................... 428/290 |
| 4,418,038 A | 11/1983 | Theeuwes ..................... 422/37 |
| 4,467,013 A | 8/1984 | Baldwin ...................... 428/289 |
| 4,919,998 A | 4/1990 | Goad et al. .................. 428/265 |
| 5,196,139 A | 3/1993 | Moschner ............... 252/186.25 |
| 5,238,463 A | 8/1993 | Arini et al. ...................... 8/111 |
| 5,490,983 A * | 2/1996 | Worley et al. ................ 424/405 |
| 5,670,646 A | 9/1997 | Worley et al. ............ 548/301.1 |
| 5,700,742 A | 12/1997 | Payne ......................... 442/123 |
| 5,882,357 A * | 3/1999 | Sun et al. ....................... 8/189 |

OTHER PUBLICATIONS

AATCC Method 114–1971, "Chlorine Retention and Scorch," Jan., 1972.
Kruschwitz, Jacqueline I., "Chloramines and Bromamines," *Encyclopedia of Chemical Technology*, 4$^{th}$ Edition (John Wiley & Sons), 1997.

\* cited by examiner

Primary Examiner—Elizabeth M. Cole
Assistant Examiner—Ula C. Ruddock
(74) Attorney, Agent, or Firm—Terry T. Moyer; William S. Parks

(57) ABSTRACT

This invention relates to antimicrobial fabrics which are treated with a specific durable and regenerable halamine/chlorine system and methods of removing residual active chlorine from the target textile surface without reducing the antimicrobial activity of the textile. Such methods comprise contacting an amine-treated fabric first with a halogen-based bleach (or other halogenated liquid) to produce halamines at the fabric surface, and subsequently washing the resultant halogenated fabric with a reducing agent which removes the residual, unbonded halogen (such as chlorine) from the fabric surface but does not, surprisingly, remove the halamine halogen. The remaining halamine halogen thus provides the desired antimicrobial activity. As a result, a method of substantially reducing fabric discoloration, odor, and potential skin irritation due to the presence of amounts of residual unbonded halogen (such as chlorine) on the target fabric surface is provided which simultaneously permits sufficient amounts of halamine halogen (such as chloramine chlorine) to remain on the target fabric for optimum microbiocidal propoerties. A fabric treated in accordance with this method is also provided.

16 Claims, No Drawings

METHOD OF RETAINING ANTIMICROBIAL PROPERTIES ON A HALAMINE-TREATED TEXTILE SUBSTRATE WHILE SIMULTANEOUSLY REDUCING DELETERIOUS ODOR AND SKIN IRRITATION EFFECTS

FIELD OF THE INVENTION

This invention relates to antimicrobial fabrics which are treated with a specific durable and regenerable halamine/chlorine system and methods of removing residual active chlorine from the target textile surface without reducing the antimicrobial activity of the textile. Such methods comprise contacting an amine-treated fabric first with a halogen-based bleach (or other halogenated liquid) to produce halamines at the fabric surface, and subsequently washing the resultant halogenated fabric with a reducing agent which removes the residual, unbonded halogen (such as chlorine) from the fabric surface but does not, surprisingly, remove the halamine halogen. The remaining halamine halogen thus provides the desired antimicrobial activity. As a result, a method of substantially reducing fabric discoloration, odor, and potential skin irritation due to the presence of amounts of residual unbonded halogen (such as chlorine) on the target fabric surface is provided which simultaneously permits sufficient amounts of halamine halogen (such as chloramine chlorine) to remain on the target fabric for optimum microbiocidal properties. A fabric treated in accordance with this method is also provided.

DISCUSSION OF THE PRIOR ART

There has been a great deal of attention in recent years given to the hazards of antimicrobial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus*, yeast, and other unicellular organisms. With such an increased consumer interest in this area, manufacturers have begun introducing antimicrobial agents, such as Triclosan, available from Ciba-Geigy under the tradename Irgasan®, within various household products. For instance, certain brands of polypropylene cutting boards, liquid soaps, etc., all contain this very effective antimicrobial compound. Generally, the incorporation of triclosan within liquid or polymeric media has been relatively simple. However, there is a long-felt need to provide effective, durable, and long-lasting antimicrobial characteristics within textiles, in particular apparel fabrics, which is extremely difficult to accomplish with triclosan. There are commercially available textile products comprising acrylic and/or acetate fibers co-extruded with triclosan (for example Hoechst Celanese markets such acetate fabrics under the name Microsafe™ and Courtaulds markets such acrylic polymer fabrics under the name Amicor™). However, such an application is limited to those types of fibers; it does not work specifically for and within polyester, polyamide, cotton, lycra, etc., fabrics.

Very recently, work has been undertaken to provide antimicrobial finishes to fabrics through the covalent bonding of certain nitrogen-containing groups, such as hydantoin, as merely one example, to individual fibers (such as cellulose fibers). Such nitrogen-containing groups (which may also include imines, amides, amines, imides, and the like) provide sites for the bonding and retention of chlorines (or other halogens) which ultimately provide the desired N-halamines which produce the desired antimicrobial characteristics. Such chlorines, and the like, are easily introduced to the textile surface through a washing process (such as with a chlorine bleach) during which some of the chlorines become bonded with the free accessible nitrogens on the hydantoins bonded to the fabric surface to produce N-halamines. Such N-halamines are, as noted above, very strong oxidants and are very effective against microorganisms. These halamines, this process, and the fabrics made thereby are more thoroughly discussed in U.S. Pat. 5,882,357 to Sun et al., herein entirely incorporated by reference and fabrics treated with certain nitrogen-containing compounds (again such as hydantoin, imines, imides, amides, and the like) are herewith denoted by the term "amine-treated fabric." This term is intended to encompass all fabrics which are treated with nitrogen-containing compounds which ultimately form of N-halamines upon contact with halogen bleaches (or other halogenated liquids, including solid bleach-containing detergents which dissolve in water to form a liquid). Such fabrics are formed in accordance with the Sun et al. patent, noted above, as an example, and the nitrogen-containing compounds include those which include triazine, hydantoin, imidazolidinone groups, and the like. The term "halamine-treated fabric" thus is intended to encompass any amine-treated fabric which has been contacted with and has retained halogens within the nitrogen-containing groups on the amine-treated fabric surface. Such halamine-treated fabric provides long-term wearability and also allows for replenishment of any removed or used antimicrobial halalamine halogen (such as chloramine chlorine). Subsequent washes with bleach, for example, will create halamines by reacting with "vacant" hydantoin groups. Thus, although the chlorine (or other halogen) may be removed or rendered unusable for antimicrobial activity, fresh supplies of chlorine, and the like, may be introduced and bonded with the hydantoin surface treatment over time to regenerate the microbiocidal capability of the target fabric.

This halamine treatment unfortunately also results in a substantial amount of adsorbed active chlorine (or other halogens) remaining on the surface of the fabric in addition to covalently bonded halamines, after each bleach (or similar halogen-containing liquid) wash. Such residual adsorbed halogen (chlorine, for instance), as is well known, produces an highly unpleasant odor, discolors fabrics, particularly those with dyes and colorants therein, and can cause irritation to a wearer's skin (if the target fabric is incorporated within apparel, for instance). Such circumstances associated with this halamine antimicrobial system have proven problematic for the incorporation of such a promising antimicrobial system and process within apparel and other textile applications in which human contact occurs. Thus, there has been noticed a necessity for providing a subsequent treatment for readily removing substantially all of the unbonded residual active chlorine (or other halogen) from the target fabric surface while also permitting the continued bonding of the antimicrobial chlorine within the halamine. Such a procedure would reduce the deleterious odor and skin irritation prevalent in the fabrics now produced with this method. However, the prior art has not provided such an improvement for halamine antimicrobial systems to date.

DESCRIPTION OF THE INVENTION

It is thus an object of the invention to provide a safe, effective procedure of removing residual adsorbed active chlorine from a halamine-treated fabric surface to substantially reduce halogen-created odors, discolorations of fabric, and potential skin irritation. Another object of the invention is to provide a process which facilitates the production of an antimicrobial fabric finish while also permitting reductions in deleterious effects related to the presence of free chlorine or other halogen molecules, and the like, on a fabric surface. Yet another object of this invention is to provide a relatively inexpensive and quick post-wash rinsing of target halamine-treated fabric which renders the fabric wearable and usable.

Accordingly, this invention encompasses a method of removing substantial amounts of residual free halogen from a halamine-treated fabric surface comprising the steps of washing an amine-treated fabric with a halogen-containing liquid and subsequently rinsing the resultant halamine-treated fabric with a reducing agent solution having a pH of from about 3 to about 12 and having an instant reactivity with the target active halogen in a standard rinsing liquid, at a temperature from about 0 to about 70° C., wherein said reducing agent does not remove an appreciable amount of active halogen molecules bonded within said halamines, thereby permitting the halamine-treated fabric to retain its antimicrobial properties. The term "antimicrobial properties" is intended to mean the ability to at least control the growth of bacteria. Thus, this term may also include a bactericide (which actually destroys bacteria). Considering the highly oxidative and reactive nature of active chlorine and other active halogen molecules, it is highly unlikely that the presence of such a reducing agent would only affect (in an appreciable manner) the free adsorbed halogens and not every oxidative halogen moiety (such as chlorine at a +1 or 0 valence state) present, whether bonded as in halamine or not, on the target fabric surface. In fact, it is well known that halamines possess similar oxidative potentials and/or reactivities with free active halogens (such as chlorines) and are used as chlorine, etc., substitutes in certain applications (such as fabric, etc., bleaches). Thus, it would be expected that since reducing agents generally react instantly (and at times violently) with highly oxidative and reactive compounds, such as free active halogens and active halamine halogens, such halogens would be removed through a rinsing step with such a reducing agent. Thus, a reducing agent rinse would theoretically render the target fabric surface antimicrobially inactive; again, unexpectedly, just the opposite appears to occur. There is no teaching nor fair suggestion within any of the prior art which would lead one of ordinary skill in the art to uncover such a phenomenon.

The proper selection of a reducing agent is made through the two parameters noted above, namely pH levels between 3 and 12, preferably from about 5 to 9, and most preferably from about 6 to about 8, and the ability to appreciable remove only free active halogens and not active halamine halogens. Any reducing agent which meets this limitation is considered to be within the scope of this inventive process. Preferably, however, specific reducing agents include sodium bisulfite, sodium thiosulfate, sodium hydrosulfide, thiourea, sodium borohydride, sodium sulfite, ascorbic acid, and the like. Of these, sodium bisulfite, being the most readily available and the least costly, has proven to be the most preferred. The reactivity of the reducing agent is generally related to the concentration of reducing agent as well. A relatively high concentration of reducing agent will remove the bonded halogens which will subsequently substantially reduce the antimicrobial activity of the target halamine-treated fabric. Thus an aqueous reducing agent solution having a concentration of from about 0.1 to about 100, preferably from about 1 to about 10 grams per gallon should be utilized in the method. Furthermore, the pH levels may be adjusted through the inclusion of a pH buffer solution (such as sodium phosphate, dibasic, as merely one possible selection) and will not affect the performance of the reducing agent in removing only unbonded active halogens (such as chlorine, bromine, iodine, and the like) from the target fabric surface.

Other additives may also be used, such as low amounts of surfactants, perfumes, antistatic agents, and the like, in order to provide other desired properties to the target fabric through a rinsing step.

Any fabric can be utilized in this invention as the important requirement is that the reducing agent be utilized in a controlled amount and concentration to effectively remove the free, potentially damaging and/or deleterious active halogens from the target fabric surface. Polyester/cotton blends are most preferred; however, any natural fibers, such as cotton, ramie, and the like; any synthetic fibers, such as polyamides, lycra, and the like; and any blends thereof of any natural and/or synthetic fibers may be utilized within the inventive fabric. Furthermore, woven fabrics are preferred; however, knitted and non-woven forms may also be utilized as well as combinations of any types of these forms. Of course, the desired fabric must be able to withstand washes with highly basic halogenated liquids ( in order to regenerate the antimicrobial activity, as noted above). Thus, white and bleach-resistant colored fabrics are preferred.

DESCRIPTION OF THE PREFERRED EMBODIMENT

The following example is indicative of the preferred embodiment of this invention and is compared with those found within the prior art:

EXAMPLE 1

A 65/35 polyester/cotton blend woven fabric was first impregnated with an aqueous solution containing about 4% by weight of 1,3-dimethylol-5,5-dimethylhydantoin and 1% by weight of magnesium chloride as a catalyst (as disclosed in U.S. Pat. No. 5,882,357 to Sun et al., noted and incorporated herein previously). The wet fabric was then dried at 250° F. for 1 minute and at 380° F. for 2 minutes. The fabric gained about 3.5% of its previous weight after this treatment. The treated fabric was then machine-washed in a regular washing cycle, followed by a bleach rinse at about 0.01% sodium hypochlorite solution (diluted commercially and available under the tradename Clorox®-brand bleach from The Clorox Company). The fabric was then rinsed with a reducing agent comprising about 0.035% sodium bisulfite in aqueous solution. The resultant fabric was then dried in a regular clothes dryer for about 40 minutes. The washed and dried fabric had no chlorine smell. Samples of this dried fabric were then tested for their antimicrobial properties against Staphylococcus aureus (ATCC 5368) and *Klebsiella pneumoniae* (ATCC 4352) using AATCC Test Method 100. The results were tabulated as follows with bacteria contact time measured at 20 hours for each:

TABLE 1

| Bacteria Type | Log reduction in bacteria | Chlorine Smell |
| --- | --- | --- |
| *Staphylococcus aureus* | >4.3 | Minimal |
| *Klebsiella pneumoniae* | >5.5 | Minimal |

These results were then compared with other untreated and treated fabrics as follows:

EXAMPLE 2 (Comparative)

The same type of fabric as in EXAMPLE 1, above, was machine-washed with the same type of bleach without first treating with an hydantoin. The washed fabric had a minimal chlorine smell.

EXAMPLE 3 (Comparative)

The same type of fabric as in EXAMPLE 1, above, was impregnated with the same hydantoin (1,3-dimethylol-5,5-dimethylhydantoin) as in the same EXAMPLE, and found to have the same approximately weight gain after treatment. The fabric was then bleach rinsed with the same Clorox®-brand bleach as in EXAMPLEs 1 and 2, and dried. The resultant fabric exhibited a very strong chlorine smell.

EXAMPLE 4 (Comparative)

The resultant fabric of EXAMPLE 2 was then rinsed with a reducing agent (the same as in EXAMPLE 1) and dried in the same manner as in EXAMPLE 2. The chlorine smell was substantially reduced.

Each of the Comparative fabrics were then made into individual samples for testing of antimicrobial activity as in TABLE 1, above (for the same types of bacteria). The results are tabulated below as follows, for contact times of about 20 hours:

TABLE 2

| Bacteria Type | Log reduction in bacteria | Chlorine Smell |
| --- | --- | --- |
| A. EXAMPLE 2 | | |
| *Staphylococcus aureus* | −0.22 | Minimal |
| *Klebsiella pneumoniae* | 0.52 | Minimal |
| B. EXAMPLE 3 | | |
| *Staphylococcus aureus* | >4.3 | Strong |
| *Klebsiella pneumoniae* | >5.5 | Strong |
| C. EXAMPLE 4 | | |
| *Staphylococcus aureus* | 0.28 | None |
| *Klebsiella pneumoniae* | 0.46 | None |

Clearly, the inventive procedure accords the same antimicrobial activity as in EXAMPLE 3 (which does not incorporate the reducing agent rinse) and also substantially reduces the undesirable chlorine odors associated with this EXAMPLE 3. Furthermore, the non-halamine treated fabrics do not exhibit any appreciable antimicrobial activity although the chlorine smell is lowered substantially for both. Thus, the inventive method provides a superior final product in both antimicrobial activity and unpleasant odor.

Test samples were then made to measure empirically the potential damage and/or discoloration to fabric due to the retention of free chlorines on the surface due to chlorine bleaching in accordance with AATCC Test Method 114-1971, "Chlorine Retention and Scorch." Strips of white polyester/cotton blend (65/35) fabric were cut (14 inches by 1-¼ inches each) and treated in accordance with Examples 1 and 3, above. The Example 3 strip exhibited an extremely strong chlorine smell while the Example 1 strip was essentially odor-free. Two heating plates were then pre-heated to about 365° F. Each strip was then placed between the two plates for 30 seconds after which the strips were removed and viewed empirically for the resultant condition of the fabric. The Example 1 strip exhibited very little discoloration; the Example 3 strip exhibited extensive browning of the fabric. Clearly, the fabric treated by the inventive process produced a more favorable result.

There are, of course, many alternative embodiments and modifications of the present invention which are intended to be included within the spirit and scope of the following claims.

What we claim is:

1. A halamine-treated, bleached fabric exhibiting antimicrobial activity through the retention of halamine-bonded chlorines, wherein, after being bleached and after being subsequently subjected to a reducing agent rinse, said fabric comprises substantially no free chlorines on its surface such that said fabric exhibits at most a minimal chlorine smell.

2. The fabric of claim 1 wherein said fabric exhibits antimicrobial log reductions for a) *Staphylococcus aureus* and b) *Klebsiella pneumoniae*, in accordance with AATCC Test Method 100, of at least a) 4.3 and b) 5.5, respectively.

3. The fabric of claim 1 wherein said fabric is of the type selected from the group consisting of woven, knit, non-woven, and any combination thereof.

4. The fabric of claim 1 wherein said fabric is comprised of fibers selected from natural, synthetic, and any blends thereof.

5. The fabric of claim 4 wherein said fabric is a blend of polyester and cotton fibers.

6. The fabric of claim 5 wherein said fabric is of the type selected from the group consisting of woven, knit, non-woven, and any combination thereof.

7. The fabric of claim 6 wherein said fabric is woven.

8. The fabric of claim 4 wherein said fabric is of the type selected from the group consisting of woven, knit, non-woven, and any combination thereof.

9. The fabric of claim 8 wherein said fabric is woven.

10. The fabric of claim 9 wherein said fabric is a blend of polyester and cotton fibers.

11. The fabric of claim 10 wherein said fabric is of the type selected from the group consisting of woven, knit, non-woven, and any combination thereof.

12. The fabric of claim 11 wherein said fabric is woven.

13. The fabric of claim 9 wherein said fabric is of the type selected from the group consisting of woven, knit, non-woven, and any combination thereof.

14. The fabric of claim 13 wherein said fabric is woven.

15. The fabric of claim 2 wherein said fabric is of the type selected from the group consisting of woven, knit, non-woven, and any combination thereof.

16. The fabric of claim 2 wherein said fabric is comprised of fibers selected from natural, synthetic, and any blends thereof.

* * * * *